United States Patent [19]

Motola et al.

[11] Patent Number: 4,975,465
[45] Date of Patent: Dec. 4, 1990

[54] ORALLY ADMINISTRABLE IBUPROFEN COMPOSITIONS

[75] Inventors: Solomon Motola, Marlton; Annabelle Mogavero, Medford; Gary R. Agisim, Cherry Hill; Pamela N. Panopoulos, Mays Landing, all of N.J.

[73] Assignee: American Home Products Corporation, New York, N.Y.

[21] Appl. No.: 329,624

[22] Filed: Mar. 28, 1989

[51] Int. Cl.⁵ ............................................. A61K 31/19
[52] U.S. Cl. .................................................... 514/557
[58] Field of Search ........................................ 514/557

[56] References Cited

U.S. PATENT DOCUMENTS 4,361,580 11/1982 Peck et al. ........................... 514/557

Primary Examiner—Nicholas S. Rizzo
Assistant Examiner—C. L. Cseh
Attorney, Agent, or Firm—John W. Routh

[57] ABSTRACT

A liquid water base ibuprofen composition for oral administration is described, the ibuprofen being maintained in suspension by a combination of primary suspending agents and being taste masked by primary taste masking agents, the composition also containing a buffer acid to adjust the pH of the composition to between 1.5 and up to about 3.5 and to provide a buffer capacity within the range of 0.03 to 0.05 between the initial pH and a pH which is 1.0 pH unit higher than the initial pH.

6 Claims, 1 Drawing Sheet

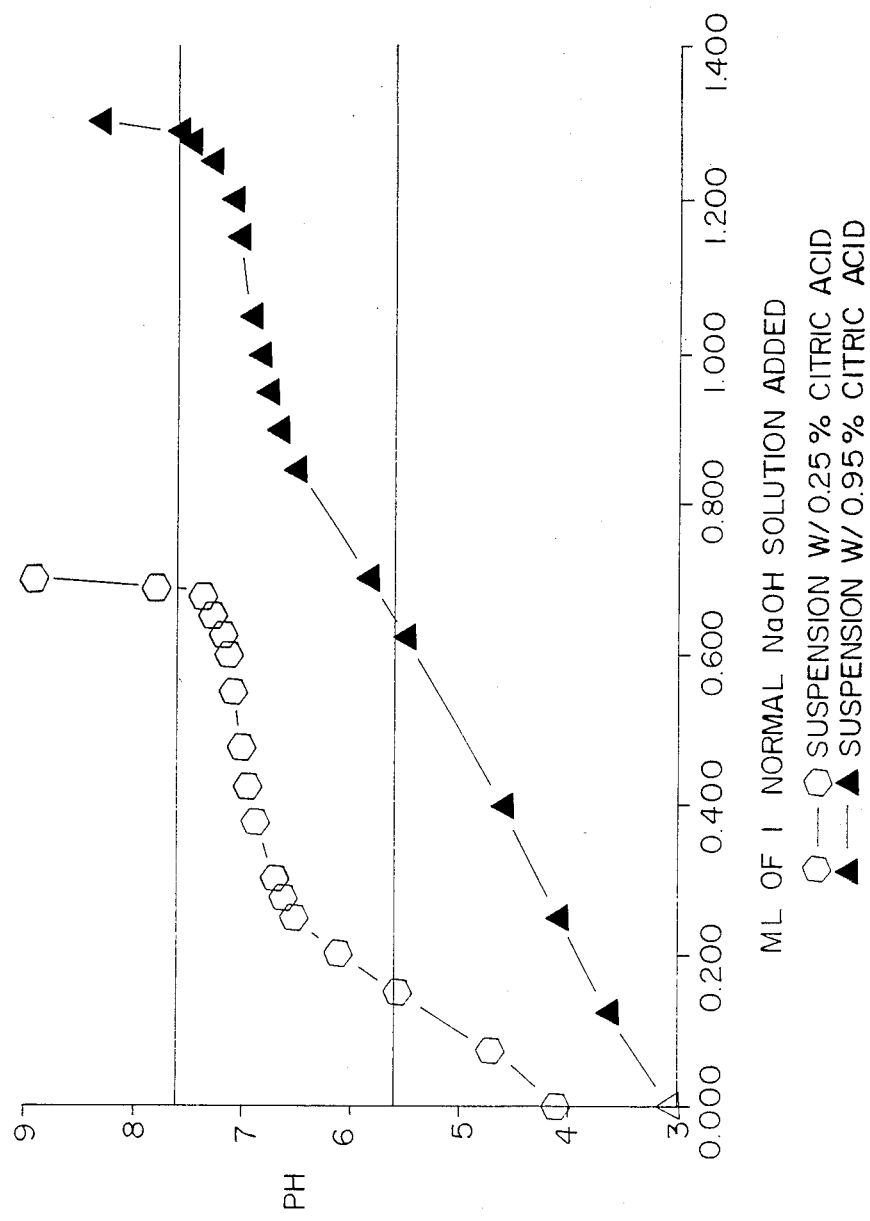

ORALLY ADMINISTRABLE IBUPROFEN COMPOSITIONS

This invention relates to a water base ibuprofen composition wherein the ibuprofen remains in suspension and wherein the bitter taste of ibuprofen is masked. More particularly the invention relates to an improved ibuprofen composition wherein the ibuprofen is maintained in suspension by primary suspending agents such as xanthan gum, microcrystalline cellulose, sodium carboxymethyl cellulose and polysorbate 80, and wherein the ibuprofen is taste-masked with taste masking agents such as sucrose and sorbitol solution, by maintaining the pH of the suspension between about 1.5 and up to about 3.5.

BACKGROUND OF THE INVENTION

Liquid ibuprofen compositions for oral administration are known in the art. One such composition is described in U.S. Pat. No. 4,684,666 as a stabilized liquid ibuprofen syrup suitable for oral administration comprising from 50 to 400 mg of ibuproen per 5 ml of syrup, the ibuprofen being suspended in an aqueous liquid having more than 50% by weight of a polyhydric alcohol bodying agent, a sweetening agent and a pH of higher than 7.0 and below 7.7. Another such composition is described in U.S. Pat. No. 4,788,220 wherein the ibuprofen is maintained in suspension by the primary suspending agents xanthan gum, microcrystalline cellulose, sodium carboxymethyl cellulose and polysorbate 80, wherein the ibuprofen is taste-masked with sucrose and sorbitol solution and the pH is maintained at about 3.5 to 5.

DESCRIPTION OF THE INVENTION

It has now been found that improved taste neutral aqueous base compositions suitable for oral administration can be formulated from ibuprofen maintained in suspension by a combination of suspending agents and also including taste masking agents by adjusting the pH of the suspension between about 1.5 and up to about 3.5 and providing a buffering capacity within the range of 0.03 to 0.05 between the initial pH of the formulation and a pH which is 1.0 pH unit higher than the initial pH.

Since ibuprofen has essentially no aqueous solubility within a pH range of 1 and 4 with a dramatic increase in solubility at pH 5, the buffering capacity of the formulation inhibits dissolution of the ibuprofen content of the suspension in the human saliva upon administration. Human saliva normally has a pH of 5.6 to 7.6 and dissolution of the ibuprofen in the saliva would contribute a bitter after taste and throat bite.

DETAILED DESCRIPTION OF THE INVENTION

The ibuprofen compositions of the invention suitable for oral administration contain about 0.8% to about 4% ibuprofen weight by volume of the total composition, about 0.1% to about 2% weight by volume of the total composition of suspension stabilizing agents, about 20% to about 70% weight by volume of the total composition of a combination of taste masking agents, about 30% to about 70% weight by volume of the total composition of water, the composition also containing citric acid or phosphoric acid in an amount of about 0.1% to about 2.0% weight by volume sufficient to adjust the pH to about 1.5 up to about 3.5, preferably about 3, and to provide a buffer capacity within the range of 0.03 to 0.05 between the initial pH and a pH which is 1.0 pH unit higher than the initial pH.

Preferably the suspending agents include xanthan gum, microcrystalline cellulose, sodium carboxymethyl cellulose and polysorbate 80. Also, preferably the taste masking agents include sucrose and sorbitol solution, although other pharmaceutacally acceptable polyols can be used such as glycerin. The buffer acids are preferably citric acid and phosphoric acid although other pharmaceutically acceptable buffer acids can be used.

The ibuprofen composition is formulated to contain about 40 mg to about 200 mg of ibuprofen per teaspoon (5 ml) of formulation, preferably about 100 mg/5 ml.

Xanthan gum is an article of commerce and is marketed by R. T. Vanderbilt Company, Inc. of Los Angeles, California under the tradename Rhodigel 23. It is a food grade thickener in powder form of about 80 mesh.

Ibuprofen is available commercially from Ethyl Corporation, Baton Rouge, Louisiana in an average particle size of 40 microns.

Microcrystalline cellulose and sodium carboxymethylcellulose are available from FMC Corporation, Newark, Delaware, the former under the brand name Avicel CL 611.

Coloring and flavoring agents can be added as desired. The other ingredients can be any national formulary or USP grades. The invention is further described by reference to the following examples.

Other suitable ingredients including other stabilizing agents are described in U.S. Pat. No. 4,684,666 herein incorporated by reference in its entirety.

EXAMPLE 1

A pediatric ibuprofen formulation was prepared having the following composition:

| Ingredient | Percent Wt/vol. | Grams per 15 liters |
|---|---|---|
| Xanthan Gum | 0.15 | 22.5 |
| Microcrystalline Cellulose | 0.75 | 112.5 |
| Sodium Benzoate, NF | 0.25 | 37.5 |
| Citric Acid Hydrous, USP | 0.95 | 142.5 |
| Sucrose, NF | 50.00 | 7500.0 |
| Glycerin, USP | 10.00 | 1500.0 |
| Sorbitol Solution, USP | 10.00 | 1500.0 |
| Ibuprofen USP | 2.0 | 300.0 |
| Sodium Carboxymethylcellulose, USP | 0.10 | 15.0 |
| Polysorbate 80, NF | 0.30 | 45.0 |
| Red FDC 40 | 0.015 | 2.25 |
| Disodium Edetate, USP | 0.05 | 7.5 |
| Artificial flavor oils | 0.16 | 24.0 |
| Purified Water Deionized, USP | qs. to 100 ml | qs to 15000 ml. |

The procedure for preparation of the above pediatric formulation is first to prepare an ibuprofen slurry. The sorbitol solution and glycerin were weighed into a jacketed kettle equipped with a stirrer. The sodium carboxymethyl cellulose was sprinkled onto the solution and mixed for 10 minutes until all of the particles were completely wet. The mixture was then heated to about 70° C. and mixed until the gum was completely hydrated. The mixture was then cooled to 45° C. and the polysorbate 80 was added. Mixing was continued while cooling the mixture to 30° C. The ibuprofen was then sprinkled slowly into the mixture and mixing was continued for 15 minutes.

The xanthan gum solution was prepared first in the form of a 1% by weight solution in water. The required amount of water was placed into a mixing bowl equipped with a Lightnin mixer and the xanthan gum slowly added and hydrated by mixing at high shear for approximately 25 minutes. Into a separate mixing vessel, equipped with a Lightnin mixer was placed a quantity of water equivalent to 30% to 40% weight by volume of the total batch (4500 to 6000 ml.). The microcrystalline cellulose was sprinkled onto the water and mixing at medium shear for 30 minutes was continued in order to completely suspended the microcrystalline cellulose. The required amount of the xanthan gum solution was added to the microcrystalline cellulose suspension with mixing for 15 minutes or until a uniform suspension was obtained.

The sucrose was then added slowly with mixing for 15 minutes, or until no sucrose particles are observed, and the coloring was added. The required amount of the ibuprofen slurry was slowly added from the first step and mixed for 15 minutes. The sodium benzoate, disodium edetate and citric acid were sequentially added and mixed for 5 minutes. The citric acid and the flavoring agents were sequentially added with mixing for 5 minutes after each addition. The remainder of the water was then added with mixing until the formulation was homogeneous.

The initial viscosity of the final formulation at 25° C. was 2800 cps with a #2 spindle at 4 RPM and standing the viscosity increased to 4800 cps which on shaking for 5 seconds decreased to 2000 cps. The initial pH of the formulation was 3.05 and the specific gravity was 1.24 gram/milliliter. The ibuprofen solubility was 0.009% weight by volume.

The formulation had a sweet, pleasant, fruity taste with no discernable unpleasant after taste or throat bite characteristic of ibuprofen.

The buffer capacity of the formulation between pH 3.0 and pH 3.5 was 0.044 and the buffer capacity between pH 3.0 and pH 4.1 was 0.044.

With this formulation the quantity of 1 Normal sodium hydroxide solution necessary to increase the pH of 5 milliliters of the formulation to the normal pH of human saliva, i.e. about pH 5.6 to about pH 7.6, is 0.63 ml to a pH of 5.6 and 1.13 ml to a pH of 7.5.

EXAMPLE 2

A pediatric ibuprofen formulation was prepared having the following composition:

| Ingredient | Percent Wt/vol. | Grams per 15 liters |
|---|---|---|
| Xanthan Gum | 0.15 | 22.5 |
| Microcrystalline Cellulose | 0.75 | 112.5 |
| Sodium Benzoate, NF | 0.25 | 37.5 |
| Phosphoric Acid, USP | 1.0 | 150.0 |
| Sucrose, NF | 50.00 | 7500.0 |
| Glycerin, USP | 10.00 | 1500.0 |
| Sorbitol Solution, USP | 10.00 | 1500.0 |
| Ibuprofen, USP | 2.0 | 300.0 |
| Sodium Carboxymethylcellulose, USP | 0.10 | 15.0 |
| Polysorbate 80, NF | 0.30 | 45.0 |
| Red FDC 40 | 0.015 | 2.25 |
| Disodium Edetate, USP | 0.05 | 7.5 |
| Artificial flavor oils | 0.16 | 24.0 |
| Purified Water, Deionized, USP | qs. to 100 ml | qs to 15000 ml. |

The procedure for preparation of the above pediatric formulation is first to prepare an ibuprofen slurry. The sorbitol solution was weighed into a jacketed kettle equipped with a stirrer. The sodium carboxymethyl cellulose was sprinkled onto the solution and mixed for 10 minutes until all of the particles were completely wet. The glycerin was added with mixing for 5 minutes and the mixture was then heated to about 70° C. the temperature held for at least 30 minutes to make sure the gum is completely hydrated and then the temperature was reduced to 45° C. The polysorbate 80 was added. Mixing was continued while cooling the mixture to 30° C. The ibuprofen was then sprinkled slowly into the mixture and mixing was continued for 15 minutes.

The xanthan gum solution was prepared first in the form of a 1% by weight solution in water. The required amount of water, 2475 grams, was placed into a mixing bowl equipped with a Lightnin mixer and 25 grams of the xanthan gum slowly added and hydrated by mixing at high shear for approximately 25 minutes. Into a separate mixing vessel, equipped with a Lightnin mixer having a large propeller was placed a quantity of water equivalent to 30% to 40% of the total batch (4500–6000 ml.). The microcrystalline cellulose was sprinkled onto the water and mixing at medium shear for 30 minutes was continued in order to completely suspend the microcrystalline cellulose. The required amount of the xanthan gum solution was added to the microcrystalline cellulose solution with mixing for 15 minutes or until a uniform solution was obtained.

The sucrose was then added slowly with mixing for 15 minutes, or until no sucrose particles are observed, and the coloring was added. The sodium benzoate and disodium edetate were sequentially added and mixed for 5 minutes. The required amount of the ibuprofen slurry was slowly added from the first step and mixed for 15 minutes. The phosphoric acid and the flavoring agents were sequentially added with mixing for 5 minutes after each addition. The remainder of the water then added with mixing until the formulation was homogeneous.

The initial viscosity of the final formulation at 25° C. was 2400 cps with a #2 spindle at 4 RPM, the initial pH of the formulation was 1.84 and the specific gravity was 1.241 gram/milliliter. On standing the viscosity increased to 4800 cps which on shaking for 5 seconds decreased to 2200 cps. The ibuprofen solubility was 0.007% weight by volume.

The formulation had a sweet, fruity taste with no discernable after taste or throat bite characteristic of ibuprofen.

The buffer capacity of the formulation between pH 1.7 and pH 2.2 was 0.059 and the buffer capacity between pH 1.7 and 2.7 was 0.046.

With this formulation the quantity of 1 Normal sodium hydroxide solution necessary to increase the pH of 5 milliliters of the formulation to the normal pH of human saliva, i.e. about pH 5.6 to about pH 7.6, is 0.50 ml to a pH of 5.6 and 0.70 ml to a pH of 6.4.

EXAMPLE 3

A formulation similar to that of Example 1 of Mody et al U.S. Pat. No. 4,788,220 was prepared as described in the patent containing 0.25% weight by volume of citric acid, 2% weight by volume of ibuprofen, 0.15% weight by volume of xanthan gum and having a pH of 4.10.

A 100 ml sample of this product was titrated with 1 Normal sodium hydroxide with pH measurements being made at each milliliter increment of sodium hydroxide up to 7.0 ml.

A 100 ml sample of Example 1 of this application was also titrated with 1 Normal sodium hydroxide with pH measurements being made at each milliliter increment of sodium hydroxide up to 7.0 ml.

The results are set forth in Table I below.

TABLE I

| Milliliters 1 N NaOH | Example 1 4,788,220 pH | Buffer* capacity | Example 1 Application ph | Buffer* capacity |
|---|---|---|---|---|
| 0.00 | 4.16 |  | 3.01 |  |
|  |  | 0.0268 |  | 0.0413 |
| 1.0 | 4.53 |  | 3.25 |  |
|  |  | 0.0216 |  | 0.0462 |
| 2.0 | 4.98 |  | 3.46 |  |
|  |  | 0.0158 |  | 0.0432 |
| 3.0 | 5.58 |  | 3.68 |  |
|  |  | 0.0165 |  | 0.0427 |
| 4.0 | 6.15 |  | 3.90 |  |
|  |  | 0.0276 |  | 0.0455 |
| 5.0 | 6.48 |  | 4.10 |  |
|  |  | 0.0562 |  | 0.0500 |
| 6.0 | 6.64 |  | 4.28 |  |
|  |  | 0.0518 |  | 0.0489 |
| 7.0 | 6.81 |  | 4.46 |  |

*Buffer capacity calcuated in accordance with method described in Physical Pharmacy, Alfred Martin et al., 3rd Edition, Lea & Febiger, Philadelphia, Pa., page 227.

Referring to Table I above, it can be seen from the data with respect to Example 1 of U.S. Pat. No. 4,788,220, that buffer capacity remained fairly constant within a range of 0.02 and 0.03 up to a pH of 5.58 (approximately the lower limit of the pH of human saliva pH 5.6) and still below 0.03 up to a pH of 6.48. Above a pH of about 6.5, the buffer capacity of above 0.05 is due to conversion of ibuprofen to the more soluble sodium salt form. Ibuprofen throat bite is least observed when ibuprofen is insoluble. With respect to Example 1 of this application, however, it can be seen that the buffer capacity remained fairly constant within a range of 0.04 to 0.05 up to a pH of 4.46.

Accordingly, the aqueous base ibuprofen compositions of this invention contain citric or phosphoric acid in an amount of about 0.1% to about 2.0% sufficient to adjust the pH to about 1.5 up to about 3.5 and to provide a buffer capacity within the range of 0.03 to 0.05 between the initial pH and a pH which is 1.0 pH unit higher than the initial pH.

The increased buffering capacity provided by the orally administrable ibuprofen formulations of this invention inhibit ibuprofen dissolution in the mouth during administration and hence the formulations exhibit negligible throat bite and a pleasant taste.

The data from Example 3 are plotted on the graph shown in FIG. 1 wherein milliliters of 1 Normal sodium hydroxide is the absissa and pH is the ordinate. Although the experimental work was done with 100 milliliters of ibuprofen formulation, the graph represents the amount of 1 Normal sodium hydroxide required to titrate a 5 milliliter (1 teaspoon) dose. The horizontal lines at pH 5.6 and 7.6 reflect the pH range of normal human saliva.

As can be seen from an examination of FIG. 1, the formulation of Example 1 of this application required more than 4 times the quantity of 1 Normal sodium hydroxide (0.646 ml.) than did the formulation of Example 1 of U.S. Pat. No. 4,788,220 to reach the saliva pH range (0.154 ml.) due to the higher buffering capacity of the formulations of this invention.

We claim:

1. A taste neutral aqueous base ibuprofen composition suitable for oral administration containing about 1% to about 4% weight ibuprofen by volume of the total composition comprising a primary suspension stabilizing combination of ingredients and a primary taste masking combination of ingredients, the suspension stabilizing combination of ingredients comprising about 0.1% to about 2% weight suspension stabilizing combination by volume of the total composition, the taste masking combination comprising about 20% to about 70% weight taste masking combination by volume of the total composition, the composition also containing citric acid or phosphoric acid in an amount of about 0.1% to about 2.0% sufficient to adjust the pH to about 1.5 up to about 3.5 and to provide a buffer capacity within the range of 0.03 to 0.05 between the initial pH and a pH which is 1.0 pH unit higher than the initial pH, and water qs to 100% by volume of the composition.

2. The ibuprofen composition of claim 1 containing citric acid or phosphoric acid in an amount of about 0.1% to about 2.0% sufficient to adjust the pH to about 3.

3. The ibuprofen composition of claim 1 also containing flavoring agents and having an ibuprofen concentration of about 50 mg to about 100 mg per 5 ml of composition.

4. The taste neutral aqueous base ibuprofen composition for oral administration of claim 2 wherein the primary suspension stabilizing combination of ingredients consists essentially of xanthan gum, microcrystalline cellulose, sodium carboxymethyl cellulose and polysorbate 80.

5. The taste neutral aqueous base ibuprofen composition for oral administration of claim 4 wherein the primary taste masking combination of ingredients consists essentially of sucrose and sorbital solution.

6. The taste neutral aqueous base ibuprofen composition of claim 3 wherein the primary taste masking combination of ingredients consists essentially of sucrose and sorbitol solution.

* * * * *